US012631579B2

(12) United States Patent
Karoum et al.

(10) Patent No.: US 12,631,579 B2
(45) Date of Patent: May 19, 2026

(54) XRF AND CALCIMETRY EVALUATION OF MULTIPHASE OILFIELD FLUIDS

(71) Applicant: Schlumberger Technology Corporation, Sugar Land, TX (US)

(72) Inventors: Reda Karoum, Houston, TX (US); Sangeeth Venugopal, Clamart (FR); Carlos Abad, Houston, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 119 days.

(21) Appl. No.: 18/825,023

(22) Filed: Sep. 5, 2024

(65) Prior Publication Data

US 2025/0076229 A1 Mar. 6, 2025

(30) Foreign Application Priority Data

Sep. 5, 2023 (EP) .................................... 23306467

(51) Int. Cl.
| | |
|---|---|
| *G01N 23/00* | (2006.01) |
| *G01N 23/223* | (2006.01) |
| *G01N 33/28* | (2006.01) |

(52) U.S. Cl.
CPC ....... *G01N 23/223* (2013.01); *G01N 33/2823* (2013.01); *G01N 2223/616* (2013.01)

(58) Field of Classification Search
CPC ........... G01N 2223/616; G01N 23/223; G01N 33/2823
See application file for complete search history.

(56) References Cited

U.S. PATENT DOCUMENTS

| | | | |
|---|---|---|---|
| 6,130,931 | A | 10/2000 | Laurila |
| 12,110,447 | B1 | 10/2024 | Ahmed |
| 2003/0101801 | A1 | 6/2003 | Wilson |
| 2008/0310588 | A1 | 12/2008 | Cooper |
| 2010/0272232 | A1 | 10/2010 | Pesce |
| 2011/0142200 | A1 | 6/2011 | Piorek |

(Continued)

FOREIGN PATENT DOCUMENTS

EP 1114310 B1 4/2012

OTHER PUBLICATIONS

Gul et al., Automated real-time solids content and salinity analysis of well construction fluids using in-line XRF measurements, Journal of Natural Gas Science and Engineering 2021 vol. 94, 7 pages.

*Primary Examiner* — Dani Fox
(74) *Attorney, Agent, or Firm* — Jeffrey D. Frantz

(57) ABSTRACT

A method for evaluating a multiphase oilfield fluid includes blending a first sample of the fluid with a viscosity modifying agent to transform the sample into a paste; making a first XRF measurement of the paste to estimate an elemental composition of the fluid; making a calcimetry measurement of a second sample of the fluid to estimate a total carbonate concentration of the fluid and to obtain an acidified second sample; separating the acidified second sample to obtain an acidified brine; making a second XRF measurement of the acidified brine to estimate an elemental composition of the acidified brine; and determining an elemental composition of a solid phase of the multiphase oilfield fluid from the elemental composition of the acidified brine and the elemental composition of the multiphase oilfield fluid.

20 Claims, 6 Drawing Sheets

(56) References Cited

U.S. PATENT DOCUMENTS

| | | | |
|---|---|---|---|
| 2014/0072095 A1 | 3/2014 | Feser | |
| 2014/0355737 A1 | 12/2014 | Korkin | |
| 2015/0330921 A1 | 11/2015 | Mazor | |
| 2017/0160081 A1 | 6/2017 | Pois | |
| 2017/0176357 A1 | 6/2017 | Pois | |
| 2018/0100290 A1 | 4/2018 | Greer | |
| 2018/0100390 A1* | 4/2018 | Patil ..................... | E21B 49/003 |
| 2023/0008196 A1 | 1/2023 | Deffenbaugh | |
| 2024/0400881 A1 | 12/2024 | Ahmed | |
| 2025/0075571 A1 | 3/2025 | Troy | |

* cited by examiner

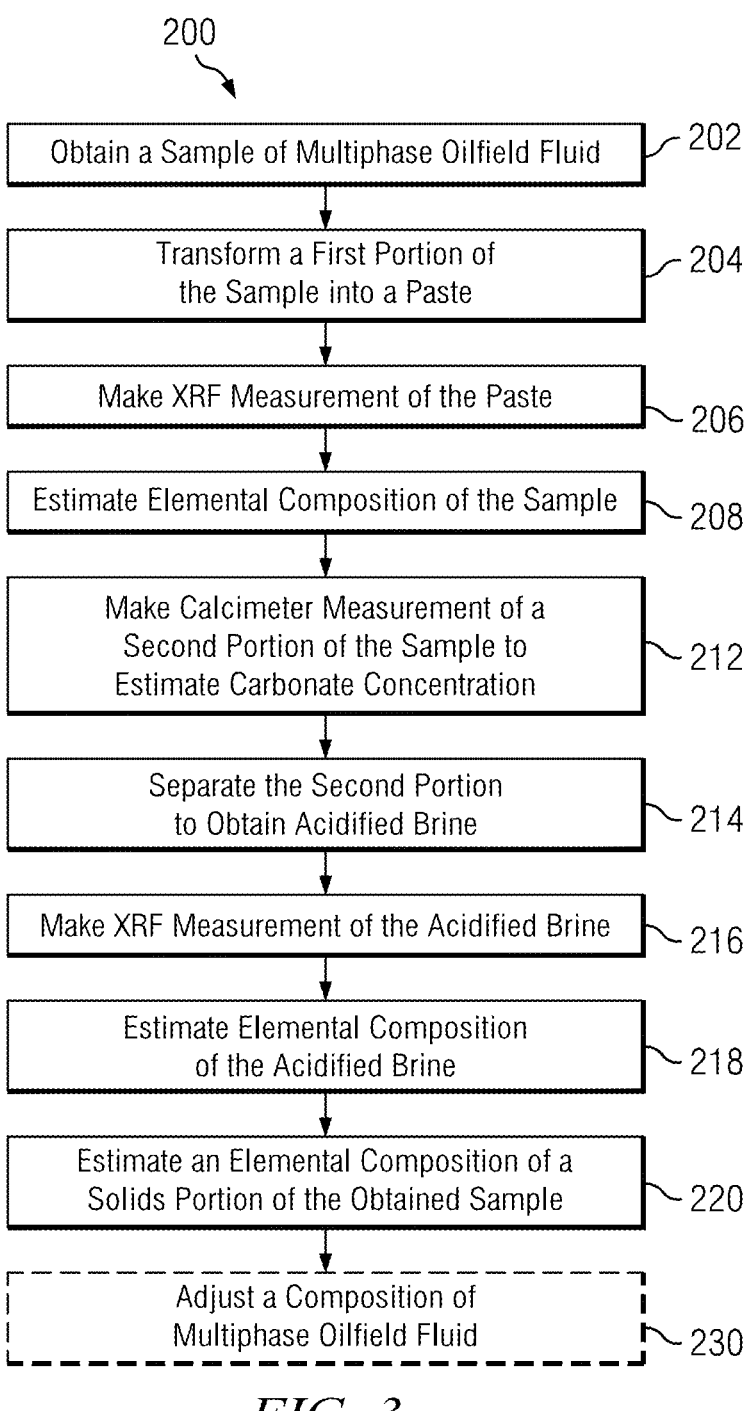

200

Obtain a Sample of Multiphase Oilfield Fluid    202

Transform a First Portion of
the Sample into a Paste    204

Make XRF Measurement of the Paste    206

Estimate Elemental Composition of the Sample    208

Make Calcimeter Measurement of a
Second Portion of the Sample to
Estimate Carbonate Concentration    212

Separate the Second Portion
to Obtain Acidified Brine    214

Make XRF Measurement of the Acidified Brine    216

Estimate Elemental Composition
of the Acidified Brine    218

Estimate an Elemental Composition of a
Solids Portion of the Obtained Sample    220

Adjust a Composition of
Multiphase Oilfield Fluid    230

*FIG. 3*

XRF AND CALCIMETRY EVALUATION OF MULTIPHASE OILFIELD FLUIDS

CROSS REFERENCE TO RELATED APPLICATIONS

This application claims the benefit of EP Application No. 23306467.4, entitled "XRF AND CALCIMETRY EVALUATION OF MULTIPHASE OILFIELD FLUIDS" filed Sep. 5, 2023, the disclosure of which is hereby incorporated herein by reference.

BACKGROUND

When drilling a well for the production of hydrocarbons, drilling fluid is often circulated through the well for a number of purposes. For example, drilling fluid is commonly intended to provide downhole hydrostatic pressure to counteract the subterranean formation pressure, cool and lubricate the drill bit, flush cuttings away from the drill bit and carry them to the surface through the wellbore annulus, and provide hydraulic power to various downhole tools. Returning drilling fluid is commonly examined at the surface to evaluate its properties and various properties of the formations surrounding the well.

As is known to those of ordinary skill, drilling fluids are highly complex, multi-phase fluids, commonly including a t least one liquid phase and one or more solid phase components. The liquid phase may be a viscosified aqueous solution of polymers or clays in brine in water-based drilling fluids (WBM), an emulsion of an aqueous fluid such as brine dispersed in an oil or diesel continuous phase in oil-based drilling fluids (OBM) or in synthetic oil-based drilling fluids (SBM) when the continuous phase is a synthetic oil, or an emulsion of an oil or diesel dispersed in an aqueous fluid such as brine (commonly referred to as a direct emulsion drilling fluid). In use, drilling fluids commonly further include drill cuttings and fine particulate matter from the formations being drilled. Monitoring changes to the drilling fluid composition can be important to predicting the performance of the fluid as well as to understanding the properties of the formations being drilled.

X-Ray Fluorescence (XRF) Spectroscopy is a well-known technique used to measure the elemental composition of a sample. For example, XRF is commonly used in oilfield applications to evaluate drill cutting samples and to determine the elemental composition of the formation rock. XRF measurements have also been proposed for use in evaluating drilling fluids. One difficulty in using XRF to evaluate drilling fluids is that drilling fluids commonly settle and undergo phase separation on the time scale of the XRF measurement. This can result in inaccurate and unreliable measurements. There remains a need in the industry for improved methods for measuring the elemental composition of in-service oilfield fluids, particularly the solid portion of the drilling fluid. Moreover, there is a need for a low cost method for making such measurements.

BRIEF DESCRIPTION OF THE DRAWINGS

For a more complete understanding of the disclosed subject matter, and advantages thereof, reference is now made to the following descriptions taken in conjunction with the accompanying drawings, in which:

FIG. 3 depicts a flow chart of one example method for estimating the elemental composition of a multiphase drilling fluid in use in a wellbore drilling operation.

DETAILED DESCRIPTION

Embodiments of this disclosure include a method and system for evaluating a multiphase oilfield fluid such as a drilling fluid or a dewatering fluid. In one example embodiment, a method includes blending a first sample of the multiphase oilfield fluid with a viscosity modifying agent to transform the first sample into a paste; making a first XRF measurement of the paste to estimate an elemental composition of the multiphase oilfield fluid; making a calcimetry measurement of a second sample of the multiphase oilfield fluid to estimate a total carbonate concentration of the multiphase oilfield fluid and to obtain an acidified second sample; separating the acidified second sample to obtain an acidified brine; making a second XRF measurement of the acidified brine to estimate an elemental composition of the acidified brine; and determining an elemental composition of a solid phase of the multiphase oilfield fluid from the elemental composition of the acidified brine and the elemental composition of the multiphase oilfield fluid.

Figure 1:
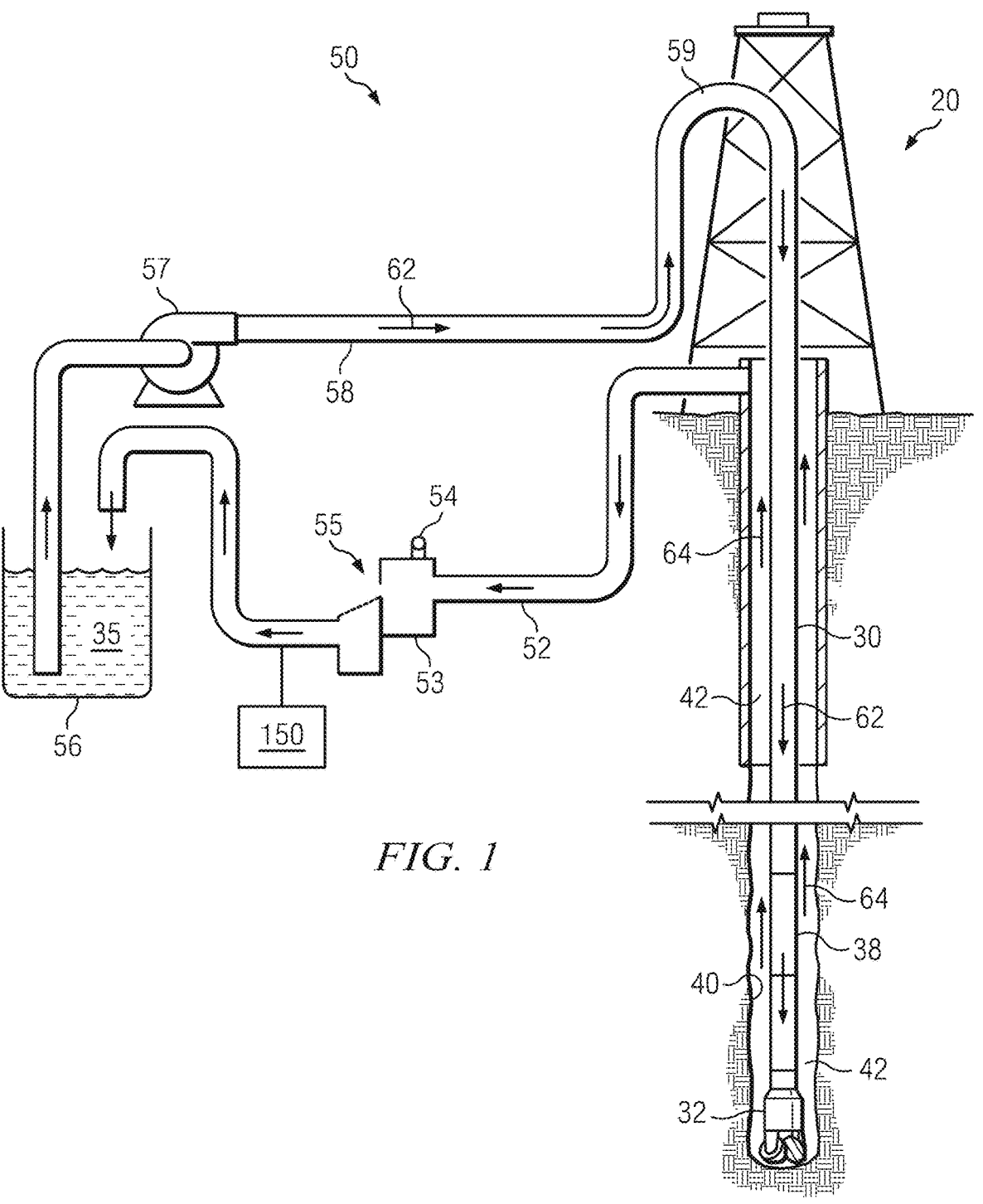
FIG. 1 depicts an example drilling rig including a system for making XRF measurements of drilling fluid in use during the drilling operation.

FIG. 1 depicts an example drilling rig 20 including a system 150 for making auto-calcimetry and XRF measurements of a water-based drilling fluid (WBM) in use during the drilling operation. The drilling rig 20 may be positioned over a subterranean formation (not shown). The rig may include, for example, a derrick and a hoisting apparatus (also not shown) for raising and lowering a drill string 30, which, as shown, extends into wellbore 40 and includes, for example, a drill bit 32 and one or more downhole measurement tools 38 (e.g., a logging while drilling tool or a measurement while drilling tool). Suitable drilling systems, for example, including drilling, steering, logging, and other downhole tools are well known in the art.

Drilling rig 20 further includes a surface system 50 for controlling the flow (or circulation) of drilling fluid 35 used on the rig (e.g., used in drilling the wellbore 40). In the example rig depicted, drilling fluid 35 is pumped downhole (as depicted at 62) via a conventional mud pump 57. The drilling fluid 35 may be pumped, for example, through a standpipe 58 and mud hose 59 in route to the drill string 30. The drilling fluid 35 typically emerges from the drill string 30 at or near the drill bit 32 (e.g., via drill bit jets) and creates an upward flow 64 of mud through the wellbore annulus 42 (the annular space between the drill string and the wellbore wall). The drilling fluid then flows through a return conduit 52 and solids control equipment 55 (such as a shale shaker) to a mud pit 56 (or mud pit system including multiple mud pits). It will be appreciated that the terms drilling fluid and mud are used synonymously herein.

The circulating drilling fluid 35 is intended to perform many functions while drilling, one of which is to carrying drill cuttings to the surface (in upward flow 64). The cuttings are commonly removed from the returning mud via a shale shaker 55 (or other similar solids control equipment) in the return conduit (e.g., immediately upstream of the mud pits 56). The drilling fluid 35 is generally reused and recirculated downhole. Formation gases that are released during drilling (along with optional tracer gases as described in more detail below) may also migrate to the surface in the circulating drilling fluid. These gasses are commonly removed from the fluid, for example, via a degasser or gas trap 54 located in or near a header tank 53 that is immediately upstream of the shale shaker 55 in the example depiction. The cuttings and gas are commonly examined at the surface to evaluate the formation layers though which the wellbore is drilled.

The drilling rig 20 further includes a system 150 for making auto-calcimetry and XRF measurements on WBM that is in use during the drilling operation. The system 150 may include an auto-calcimetry measurement apparatus and an XRF measurement apparatus and may be located, for example, in an onsite laboratory. The system may alternatively be located within the surface system 50, for example, in fluid communication with the return conduit 52 and/or the mud pit(s) 56. Drilling fluid samples may be obtained from substantially any suitable location or locations in the surface system, for example, along the return conduit 52, between the shale shaker 55 and the mud pit 56 as depicted, in fluid communication with the mud pit 56, or along standpipe 58 or mud hose 59. The disclosed embodiments are not limited in this regard. As described in more detail below with respect to FIGS. 3-5, the system 150 may be configured to receive a sample of drilling fluid, prepare a portion of the sample for XRF evaluation, make the XRF measurements on the prepared sample, and make auto-calcimetry measurements on another portion of the sample.

While FIG. 1 depicts a land rig 20, it will be appreciated that the disclosed embodiments are equally well suited for land rigs or offshore rigs. As is known to those of ordinary skill, offshore rigs commonly include a platform deployed atop a riser that extends from the sea floor to the surface. The drill string extends downward from the platform, through the riser, and into the wellbore through a blowout preventer (BOP) located on the sea floor. The disclosed embodiments are not limited in these regards.

Figure 2:
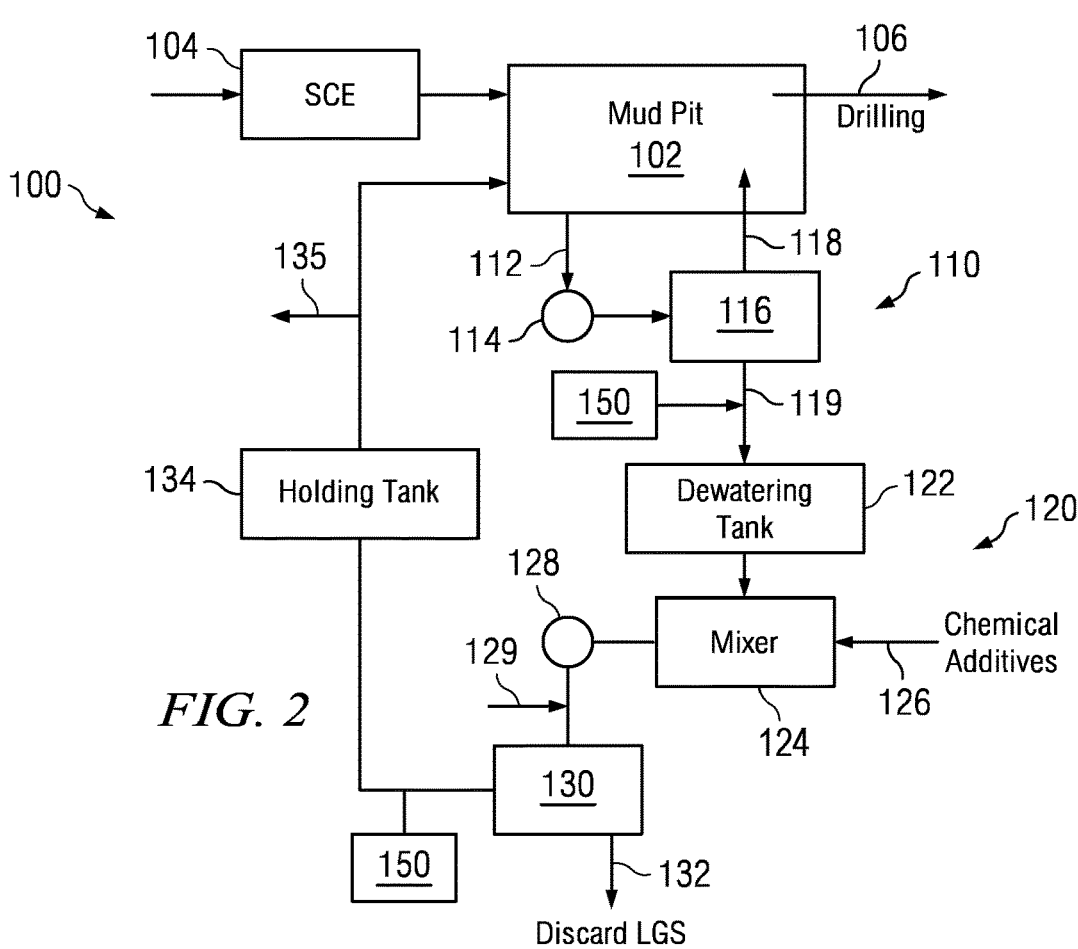
FIG. 2 depicts a process diagram for an example dewatering process including a high gravity solids recovery system and low gravity solids removal system for an example drilling fluid.

FIG. 2 depicts a process diagram 100 for one example WBM dewatering process including a high gravity solids (HGS) recovery system 110 (e.g., for the recovery of large particles and HGS such as barite) and a low gravity solids (LGS) removal system (e.g., for removal of small particles and LGS such as silicas and clays). The depicted example process diagram 100 includes a system 150 for making auto-calcimetry and XRF measurements deployed in the HGS recovery system 110 and the LGS removal system 120.

In the depicted example, drilling fluid flows into a mud pit 102 (or mud pit system) from solids control equipment 104 (e.g., a shale shaker) where it may be adjusted or modified prior to being pumped downhole at 106. Drilling fluid is received from the mud pit 102 into an HGS recovery system 110, for example, via flow line 112 and pump 114 (e.g., a centrifugal pump). The received drilling fluid is pumped through an HGS recovery centrifuge 116 which is configured to remove a portion of the HGS (e.g., barite) from the drilling fluid and return the recovered HGS (the centrifugate) to the mud pit as depicted at 118. The supernatant 119

(also referred to herein as a dewatering fluid) may be transferred to the LGS removal system 120 (also referred to as a dewatering system), for example, via storage tank 122. As described in more detail below, the HGS recovery system 110 may optionally include one or more XRF/auto-calcimetry measurement systems 150.

As used therein the term high gravity solids (HGS) refers to dense solids, such as barite, calcium carbonate, and/or hematite, that are added to the drilling fluid to increase the density thereof. HGS are also commonly referred to in the art as weighting material and often have a density exceeding 4 $g/cm^3$. As used herein the term low gravity solids (LGS) refers to dispersed lower density solids not trapped in the solids control shakers such as finely ground, drill cuttings and or added clay (e.g., bentonite clay). It will be appreciated by those of ordinary skill in the art that the HGS recovery system 110 may be configured to substantially remove HGS from the drilling fluid (in the centrifugate), while substantially leaving the LGS in the supernatant. For example, the flow rate of the drilling fluid and the rotation rate of the centrifuge may be adjusted (optimized) such that the centrifuge removes primarily (or mostly) HGS. Therefore, in many operations, drilling fluid in the dewatering storage tank 122 generally includes LGS (and a small amount of HGS).

Drilling fluid in the storage tank 122 may be transferred to mixer 124 (e.g., a static mixer or blender). Water and one or more chemical additives in aqueous solutions, such as a coagulant and/or an acid may be added to the mixer as depicted at 126. After mixing in the additive(s), the drilling fluid may be pumped 128 through a dewatering centrifuge 130 that is configured to concentrate and remove the LGS (and any remaining HGS) at 132. As depicted, one or more polymer additives 129 (flocculants dissolved in water) may be injected into the drilling fluid prior to centrifugation, often with some pipe or tank residence time to allow them residence time to increase their effectiveness, and enhance the particle agglomeration/flocculation and the separation in the centrifuge. The supernatant (also referred to as clean centrate) may then be transferred to holding tank 134, where it may be optionally further treated, diluted, etc. prior to recycling back into the mud pit 102, or may be considered as an excess, and disposed from the process 135. As also described in more detail below, the dewatering system 120 may optionally include one or more XRF/auto-calcimetry measurement systems 150.

With continued reference to FIG. 2, fluid samples may be obtained at substantially any suitable locations in the HGS recovery system 110 and/or the dewatering system 120, and evaluated using calcimetry and XRF measurements, for example, as described in more detail below with respect to FIGS. 3-5. In example embodiments, a fluid sample may be obtained from the supernatant of the HGS recovery centrifuge 116. The acquired XRF spectra may then be evaluated, for example, for the presence of barium, manganese iron, or calcium to indicate the amount of HGS (e.g., barite, hematite, manganese oxide, or in some cases calcium carbonate, or calcium/magnesium carbonate, or any other high specific gravity solids that could be used in the drilling fluid) remaining in the supernatant (e.g., to determine the effectiveness of the HGS recovery operation). It will be understood that high concentrations of HGS in the supernatant may indicate an inefficient HGS recovery operation while low concentrations of HGS in the supernatant may indicate an efficient HGS recovery operation. Moreover, it will further be appreciated that the drilling fluid flow rate through the centrifuge and the rotation rate of the centrifuge may be adjusted in response to the XRF measurements.

In other example embodiments, a fluid sample (or another fluid sample) may be obtained from the supernatant of the dewatering centrifuge 130. The acquired XRF spectra may then be evaluated, for example, for the presence of calcium, magnesium, silicon, aluminum, thorium, uranium, etc. to indicate the amount of LGS (e.g., formation minerals, silica, feldspar and clay) remaining in the supernatant (e.g., to determine the effectiveness of the LGS removal operation). It will be understood that high concentrations of LGS in the supernatant may indicate an inefficient dewatering operation while low concentrations of LGS in the supernatant may indicate an efficient dewatering operation. Moreover, it will further be appreciated that the fluid flow rate through the centrifuge, the rotation rate of the centrifuge, and the mass of chemical additives (e.g., flocculant or coagulant) added to the mixer may be adjusted in response to the XRF measurements.

With still further reference to FIG. 2, the XRF measurements may be evaluated for the presence of the flocculant or coagulant in the supernatant. In some dewatering operations, the flocculant may include aluminum sulfate or aluminum chloride, or aluminum polychloride. In such operations it may be undesirable to recycle aluminum into the mud pit, as this could cause deleterious effects to the drilling mud viscosity. XRF measurements of the supernatant from the dewatering centrifuge 130 may be evaluated for the presence of aluminum in the stream, and the measurement be used to control the amount of coagulant and flocculant added to the mixer. Those of skill in the art will appreciate that selecting the appropriate level of aluminum carryover implies a balance between the amount of LGS solids returned to the pit, and the extend of the removal of solids and other drilling mud chemicals through the coagulation and flocculation process, which is best optimized for each drilling fluids, operation and rig, as needed.

As noted above, drilling fluid samples may be obtained at substantially any suitable locations in the HGS recovery system 110 and/or the dewatering system 120. Other suitable locations may include, for example, the inputs to and the centrifugate outputs from the HGS recovery centrifuge 116 and the dewatering centrifuge 130 as well as the return line to the mud pit 102. It will be appreciated that acquiring drilling fluid samples from each of the inputs to and centrifugate and supernatant outputs from the centrifuges 116, 130 may advantageously enable a mass balance to be determined (estimated) for each centrifuge. Such a mass balance may determine the effectiveness of the centrifuge at removing the HGS and LGS from the drilling fluid.

It will be appreciated that during drilling operations, and notably when WBM are used, the drilling fluid may include various alkaline earth materials, such as magnesium, calcium, strontium, and barium containing compounds. Such compounds may be intentionally introduced to the drilling fluid, but may also be introduced from the formation being drilled. The alkaline earth metals may be present as compounds such as a barite or calcite or as divalent cations. For a drilling engineer on a rig, it is important to properly manage or control the amount of alkaline earth containing materials in the drilling fluid. Such control may include adding alkaline earth compounds to the drilling fluid, such as barite, calcite, or marble solids (calcium carbonate), pH control agents, such as lime (calcium oxide), or a brine including calcium chloride or calcium bromide. Control of the alkaline earths may further include controlling the apparent removal thereof from the fluid (e.g., through dilution) or the effective removal thereof (e.g., through enhanced solids management, changing the gage of the shakers, or through dewatering operations).

As an example of the above, WBM commonly includes barite (barium sulfate) as a weighting agent (some traces of barium carbonate may also be present). Similarly, and in trace levels, celestine (strontium sulfate) or even strontium carbonate may be present in the weighting agent added to the drilling fluid. Such weighting agents may be added to the WBM from time to time to compensate for lost material during the drilling operation.

Further, calcium containing compounds may also be added to the WBM, for example, including calcite powder (calcium carbonate) for fluid loss, or as a weighting material for reservoir drilling fluids, marble, or dolomite (calcium-magnesium carbonate). Other calcium containing compounds may be added for pH maintenance, for example, including calcium hydroxide, calcium peroxide, or lime. Calcium containing compounds native to the formation may also be picked up during drilling when drilling through carbonate formations such as calcite, chalk, and/or dolomite, or through carbonate rich carbonaceous shales. Moreover, calcium sulfate can be picked-up during the drilling process, when drilling through calcium sulfate formations such as anhydrite. Other calcium rich minerals may also be picked-up during drilling, for example, including plagioclase (a calcium containing feldspar), calcium containing chlorites, and other calcium rich clays, etc. Calcium can be also be picked-up through drilling cemented wellbores, such as after each new string is started, or when drilling a side track through a kick-off plug. Furthermore, calcium carbonate can be formed in-situ by a reaction between calcium cations and carbonate or bicarbonate anions in the fluid.

Still further, magnesium containing compounds may also be added to the WBM, for example, including dolomite. Other magnesium species, such as magnesium oxide or magnesium peroxide, may also be added. Magnesium compounds in the formation, such as dolomites or carbonate rich carbonaceous shales, can also be picked-up during the drilling process. Moreover, magnesium carbonate can be formed in-situ by a reaction between magnesium cations and carbonate or bicarbonate anions in the fluid.

Ultimately, the drilling engineer is faced with multiple decisions that depend on the chemical nature (and in particular the composition) of the WBM. The decisions related to the concentration of weighting agent, such as barite, are commonly based on measurements of fluid density, but may be advantageously supported with compositional measurements from various outlet streams, such as the centrifuges used for barite recovery and dewatering. Decisions related to calcium control are generally more complex, and may advantageously benefit from additional chemical measurements (beyond the traditional calcium titration).

FIG. 3 depicts a flow chart of one example method 200 for evaluating a multiphase water-based oilfield fluid in use in a wellbore drilling, completion, or other oilfield operation. The method includes receiving (or obtaining) a sample of the oilfield fluid at 202 (or obtaining first and second samples). During an example drilling operation, the samples may be obtained from substantially any location in the surface system 50, for example, from the return conduit 52, the shale shaker 55, the mud pit 56, standpipe 58, or mud hose 59 (FIG. 1). In certain advantageous embodiments, the samples may be obtained from the return conduit 52 upstream of the mud pits. The sample may also be obtained during a completion operation or from a HGS recovery system or dewatering system as described above with respect to FIG. 2.

With continued reference to FIG. 3, a first portion of the sample (or a first sample) is blended with a viscosity modifying agent including a high surface area powder such as carbon black to transform the sample to a high viscosity paste (or paste-like sample) at 204. XRF measurements may then be made on the paste at 206 to determine the elemental composition of the whole fluid at 208. By whole fluid it is meant the whole multiphase fluid including both the solid and liquid portions thereof.

A second portion of the sample (or a second sample) is evaluated with a calcimeter (e.g., an auto-calcimeter) at 212 to determine a concentration of carbonates therein (e.g., a total carbonate concentration). The acidified sample may then be separated, for example, via screening or filtering to obtain an acidified water-based brine (e.g., a filtrate) at 214. In certain embodiments the use of a screen or press may be advantageous that it is readily available at the rig site and may be inexpensively employed. XRF measurements are then made on the acidified water-based brine (e.g., the filtrate) at 216 to obtain an elemental composition thereof at 218. The elemental compositions of the whole fluid (the first portion) measured at 206 and the brine (the second portion) measured at 216 may then be evaluated at 220 to estimate the elemental composition of the solids in the original sample(s) (in the multiphase fluid). For example, the elemental composition of the brine may be subtracted from the elemental composition of the whole fluid to obtain the elemental composition of the solids. The evaluation may further include subtracting a measured or known elemental composition that was added to the multiphase fluid during the auto-calcimetry measurements (e.g., chorine added from the use of hydrochloric acid).

Method 200 may further optionally include modifying or adjusting the composition of the drilling fluid or changing the drilling parameters (such as the flow rate, weight on bit, or rotation rate of the drill string) at 230. For example, the quantity of some of the drilling solids, often called high gravity solids (HGS) (such as barite or calcite) in the suspended solids may be compared with a desired amount. Additional HGS may be added when the amount falls below a predetermined threshold.

In another example, high amounts of aluminium, thorium, and uranium may indicate a high level of argillaceous matter (such as clay) in the suspended solids that can lead to bit balling. A drilling operator may elect to reduce the weight on bit or increase the drilling fluid flow rate in response to such indications. Alternatively and/or additionally, the drilling operator may elect to add a shale inhibitor to the drilling fluid.

In still another example, high amounts of silicon with lower amounts of thorium and uranium may indicate a high level of sandstone and/or siltstone with a corresponding higher risk of abrasion. A drilling operator may elect to dilute the drilling fluid (e.g., by adding additional water) or adding a lubricant to the drilling fluid.

The elemental composition of the whole fluid, the brine, or the solids may also be evaluated to adjust a dewatering process (e.g., the HGS recovery system or the LGS removal system), for example, as described above with respect to FIG. 2. For example, the flow rate of the drilling fluid and/or the rotation rates of the centrifuges 116 and 130 may be adjusted or optimized to adjust the amount of HGS or LGS removed from the fluid.

Figure 4:
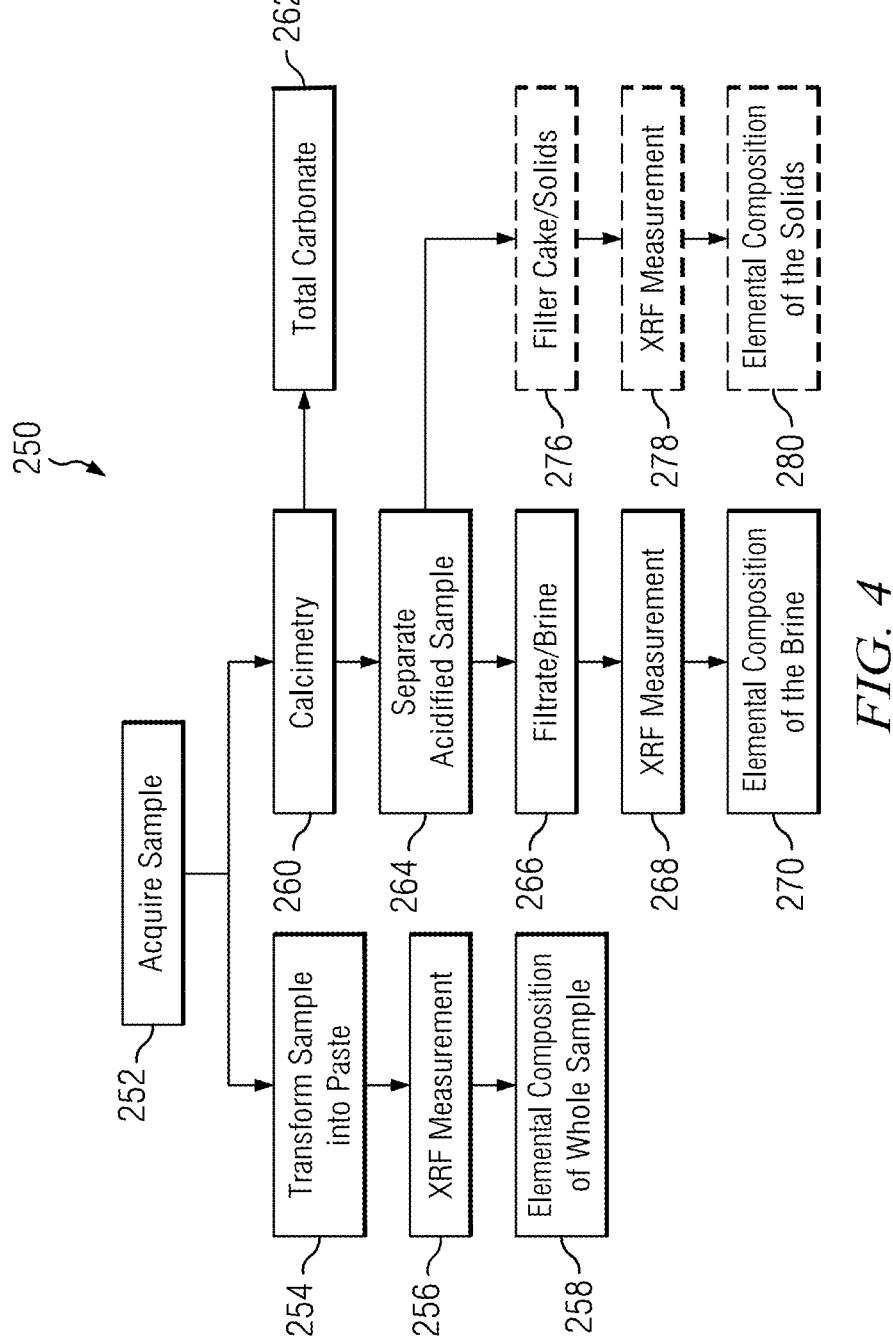
FIG. 4 depicts a flow chart of another example method for estimating the elemental composition of a multiphase drilling fluid in use in a wellbore drilling operation.

FIG. 4 depicts a flow chart of another example method 250 for evaluating the composition of an oilfield fluid. A sample of the fluid is acquired at 252, for example, as described above with respect to FIG. 3. A first portion of the acquired sample is transformed into a paste at 254, for example, by blending the sample portion with carbon black. An XRF measurement of the paste is made at 256 and evaluated to obtain an elemental composition of the whole fluid sample at 258.

A second portion of the acquired sample is evaluated using calcimetry or auto-calcimetry at 260 to determine the total amount of carbonate in the sample at 262. As described above, the calcimetry measurements involve adding an acid to the sample and measuring the volume or pressure of carbon dioxide that is generated. Substantially any suitable acid may be used, for example, including inorganic acids such as hydrochloric, hydrofluoric, nitric, sulfuric, and phosphoric acid, as well as organic acids including methane sulfonic, formic, acetic, glycolic, lactic, and citric acid. The disclosed embodiments are not limited in these regards. The acidified sample may be separated at 264, for example, via pressing the sample through a screen, a sieve, or a filter cartridge to obtain a liquid filtrate (brine) sample at 266. An XRF measurement of the acidified brine is made at 268 and evaluated to obtain an elemental composition of the acidified brine at 270.

As described above with respect to FIG. 3, the elemental composition of the brine obtained at 270 may be adjusted to account for the added acid (for example via subtracting chlorine from the composition). The adjusted composition of the brine may then be subtracted from the elemental composition of the whole sample obtained at 258 to obtain an estimated elemental composition of the solids in the fluid. In optional embodiments, the solids or filter cake 276 may be acquired from the separation in 264. An XRF measurement may be optionally made on these solids at 278 and evaluated to obtain an elemental composition of the solids in the oilfield fluid at 280. Moreover, the estimated composition of the solids obtained via subtraction may be compared with a measured composition of the solids obtained at 280 to further evaluate the composition of the fluid.

It will be appreciated that performing such analysis may provide a drilling or mud engineer with additional information to elucidate the amount of carbonate present in the sample, and other solids, and minerals notably containing calcium, so as to make appropriate decisions with respect weighting solids, fluid loss, pH control, calcium control, solids control, HGS and LGS removal efficiency, dilution, and other additive concentration.

With continued reference to FIGS. 3-4, the above described XRF and calcimetry measurements may be repeated with depth or time during a drilling operation to monitor changes in fluid composition. The composition of the fluid may then be in adjusted in response to observed changes. For example, additional HGS may be added when the amount of barium or calcium is decreasing with time or depth. Alternatively, the HGS recovery process may be adjusted. In another example, increasing amounts of aluminium, thorium, and uranium may indicate an increasing level of argillaceous matter (such as clay) in the suspended solids. A drilling operator may elect to reduce the weight on bit or increase the drilling fluid flow rate in response to such indications. Alternatively and/or additionally, the drilling operator may elect to add a shale inhibitor to the drilling fluid. In still another example, increasing amounts of silicon with lower amounts of thorium and uranium may indicate increasing levels of sandstone and/or siltstone with a corresponding higher risk of abrasion. A drilling operator may elect to dilute the drilling fluid (e.g., by adding additional water) or adding a lubricant to the drilling fluid response to such changes.

With continued reference to FIGS. 3-4, it will be appreciated that blending the drilling fluid sample with the viscosity modifying agent increases the viscosity of the sample significantly, thereby preventing (or significantly delaying or slowing) phase separation and settling of the high-density components in the fluid. It will be appreciated that settling of solids in a multi-phase fluid is a kinetic process and that adding the viscosity modifying agent is intended to reduce the settling velocity of the solids. Reducing the settling velocity may be achieved, for example, via increasing the viscosity of the fluid at low shear rates and/or by providing the fluid with a large yield stress. In example embodiments, a viscosity of greater than about 100 P, or 10 Pa s at low shear rates such as 1 $s^{-1}$, may be sufficient to prevent settling in the drilling fluid in the time frame required to obtain an XRF measurement (e.g., greater than about 200 P, greater than about 500 P, or greater than about 1000 P). In terms of yield stress, a yield stress of greater than about 10 Pa may be sufficient to prevent settling in the drilling fluid in the time frame required to obtain an XRF measurement (e.g., greater than about 20 Pa, greater than about 50 Pa, or greater than about 100 Pa).

In advantageous embodiments, a sufficient quantity of a high surface area powder is added to the sample so as to transform the sample into a paste. The quantity of powder added to the drilling fluid sample generally depends on the mass (or volume) of the sample, the type of fluid, and the type of powder used. In example embodiments in which the high surface area powder is carbon black, the quantity of the powder may range from a weight ratio of 10 parts powder to 1 part oilfield fluid (10:1) to a weight ratio of 1 part powder to about 100 parts oilfield fluid (1:100). For example, in some applications, it may be advantageous to provide a high dilution factor for evaluating highly concentrated elements or elements that have partially overlapping peaks. In such embodiments, a weight ratio in a range from about 10 parts powder to 1 part oilfield fluid (10:1) to about 1 part powder to about 1 part oilfield fluid (1:1) may be advantageous. In other example applications, it may be advantageous to use as little of the powder as possible to obtain a high viscosity paste. In such embodiments, a weight ratio in a range from about 1 part powder to about 1 part oilfield fluid (1:1) to a about 1 part powder to about 100 parts oilfield fluid (1:100) may be advantageous (e.g., from about 1:2 to about 1:50, from about 1:3 to about 1:19, or from about 1:3 to about 1:9). In still other example applications, for example, in which the oilfield fluid has a high initial viscosity, a weight ratio in a range from about 1 part powder to about 20 parts oilfield fluid (1:20) to a about 1 part powder to about 100 parts oilfield fluid (1:100) may be advantageous. In one example embodiment, 1 part by weight carbon black is added to 4 parts by weight drilling fluid. In another example embodiment, one part by weight carbon black is added to 9 parts by weight drilling fluid.

The viscosity modifying agent may include substantially any suitable powder, for example, including carbon black, fumed silica, alumina, and other powders. Carbon black, particularly high surface area carbon black, may be advantageously utilized since small amounts of carbon black can significantly increase the sample viscosity and promote paste formation. Moreover, carbon black (being essentially entirely carbon) is advantageously undetectable to the XRF measurements and therefore does not influence the estimated elemental composition of the drilling fluid. Of course, it will be understood that carbon black may include trace impurities. These impurities may be ignored in some operations. In other operations it may be advantageous to measure an XRF spectrum of carbon black and subtract (or otherwise account for) any impurities in the subsequent spectra obtained from the paste samples.

It will be appreciated that substantially any suitable carbon black may be utilized, for example, having a surface area in a range from about 80 $m^2/g$ to about 1000 $m^2/g$. While higher surface area carbon blacks may be advantageous in that less of the carbon black is required to achieve a high viscosity paste, the disclosed embodiments are explicitly not limited in this regard.

With still further reference to FIGS. 3-4, advantageous embodiments of method 100 may be automated or semi-automated. For example, a first drilling fluid sample may be automatically pumped from one of the flow lines or from the mud pit (FIG. 1) to a blender (mixer). The carbon black (or other powder) may be automatically metered into the blender either before or after the drilling fluid sample is received and then automatically blended with the powder. After blending the paste may be automatically injected (or otherwise transferred) into a sample cup (or holder), which may in turn be automatically or manually transferred to the XRF chamber for measurement. The XRF measurement may be automatically or manually triggered and the corresponding spectrum saved and evaluated on a computer.

A second portion of the sample (e.g., a second sample) may be automatically pumped from one of the flow lines or from the mud pit (FIG. 1) to an auto-calcimeter to estimate a total carbonate concentration in the sample. In addition to the auto-calcimeter, calibrated Draeger tubes can be used to further estimate the carbonate concentration in the sample. The acidified sample may then be automatically or manually pressed through a screen, a sieve, or a filter cartridge to obtain a liquid filtrate (brine) sample. The acidified sample may alternatively be transferred to a centrifuge to obtain a supernatant (brine) sample. The brine sample may then be automatically or manually transferred to the XRF apparatus to obtain an XRF measurement.

With still further reference to FIGS. 3-4, the calcimetry measurements may be made at 212 and 260 using substantially any suitable calcimeter or auto-calcimeter. In one example calcimeter measurement, a fixed quantity of acid (such as HCl) is added to the sample and a corresponding carbon dioxide pressure is measured. The amount of carbonate compounds in the sample may be determined from the pressure (e.g., from a correlation or a calibration curve).

Figure 5:
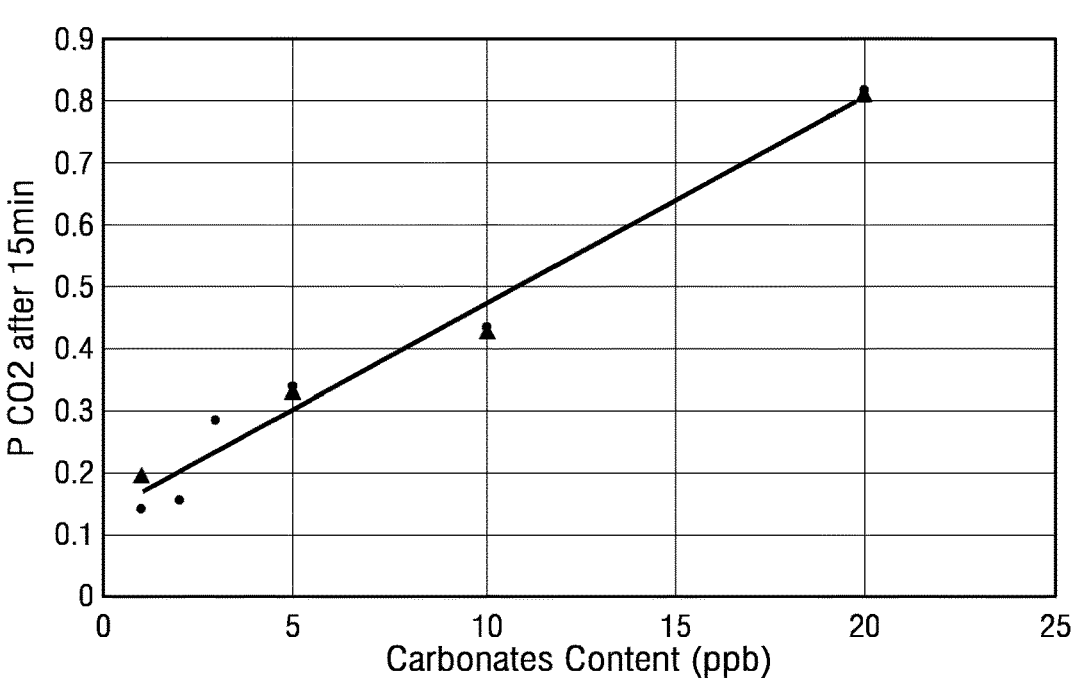
FIG. 5 depicts a plot of carbon dioxide pressure versus the concentration of carbonates in a drilling fluid sample.

FIG. 5 depicts a plot of carbon dioxide partial pressure (in units of psi) obtained fifteen minutes after adding hydrochloric acid (10 wt. % HCl) to a sample of WBM versus the concentration of carbonates in the sample (in units of pounds per barrel) Note that in this example the pressure is linearly proportional to the carbonate concentration. In example embodiments, the calcimeter (or auto-calcimeter) may be configured to add a predetermined volume of an acid (such as HCl) to the sample and to estimate the carbonate concentration from a pressure measurement (a carbonate pressure).

Figure 6:
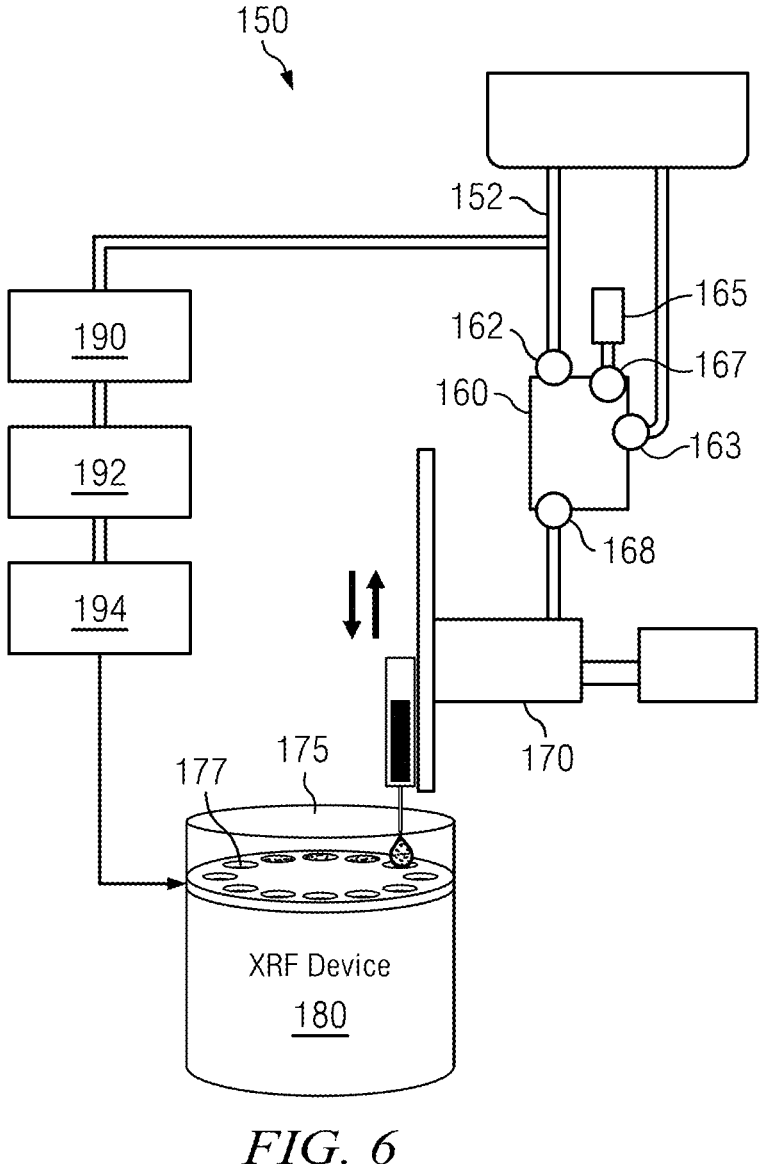
FIG. 6 depicts one example embodiment of an XRF measurement system for making XRF measurements on drilling fluid that is in use during the drilling operation.

FIG. 6 depicts one example embodiment of a system 150 for making XRF and calcimetry measurements on an oilfield fluid that is in use during a drilling operation (e.g., as in FIG. 1) or a dewatering process (e.g., as in FIG. 2). In the depicted embodiment, a fluid inlet port 152 is in fluid communication with a mud pit 56 or a fluid flow line, for example, including return conduit 52, standpipe 58, mud hose 59, or the flow line between the shale shaker 55 and the mud pit 56 (FIG. 1). The sample may also be obtained during a completion operation or from a HGS recovery system or dewatering system as described above with respect to FIG. 2. A mixer (or blender) 160 is in fluid communication with the inlet port and a carbon black (or other powder) tank 165 and an XRF sample dispenser 170. A sample of drilling fluid may be drawn or received into the blender 160 by opening valve 162 and closing valve 163. Carbon black may be added to the blender 160 from the carbon black tank by opening a metering element 167, including, for example, a valve, an auger, an Archimedes screw, an extruder, a twin extruder, a solid shaker, or any other solid powder metering device.

The blender 160 may be configured to shear the contents thereof and thereby transform the carbon black drilling fluid sample mixture into a high viscosity fluid or paste. The resulting paste may be transferred to the sample dispenser 170 by opening valve 168. The dispenser may include a motorized syringe 172 configured to dispense a predetermined volume of the paste into sample holder 175. The sample holder may include a plurality of sample cups 177, arranged, for example, in a circular carousel. The individual samples may be rotated (one by one) through the XRF apparatus 180 to obtain corresponding XRF measurements of the samples. It will, of course, be appreciated that the system 150 (or portions thereof) may be rinsed, for example, using a base oil to avoid cross contamination between measurements.

With continued reference to FIG. 6, the XRF instrument 180 may include substantially any suitable XRF device, for example, including a portable device such as the Epsilon 1 available from Malvern® Instruments. In example embodiments, the XRF instrument 180 may include a vacuum pump and vacuum sample chamber for making XRF measurements under vacuum (or low pressure), an X-ray tube, a Si-drift detector, corresponding electronics, and a temperature controller for controlling the temperature of the sample chamber. The XRF instrument 180 may be integrated with the sample carousel for making automated or semi-automated measurements.

With still further reference to FIG. 6, the inlet fluid port may be in further fluid communication with an auto-calcimeter 190. As described above, the auto-calcimeter is configured to estimate the total carbonate in the multiphase fluid by acidifying the fluid and measuring a corresponding pressure of carbon dioxide. The auto-calcimeter 190 may be configured to measure various fluid properties prior to making the calcimeter measurement, for example, including density, pH, and temperature. A fluid sample may be received in a calcimeter chamber where it is acidified (e.g., by adding a predetermined volume or mass of HCl). The corresponding increasing pressure in the chamber may be monitored using a pressure sensor. A valve may be opened when the pressure sensor measurements stabilize thereby routing the generated gas to a Draeger tube to obtain an accurate measurement of the partial pressure of carbon dioxide.

The auto-calcimeter 190 may be in further fluid communication with a separation apparatus 192 such as a screen, a sieve, a filter, or a centrifuge configured to separate the acidified multiphase fluid into an acidified brine and solids portions (e.g., to remove solids from the acidified multiphase fluid, thereby leaving acidified brine). The resulting acidified brine may be received by a liquid sample holder 194 (e.g., a sample cup or container) and transferred to the XRF apparatus 180 to obtain corresponding XRF measurements of the acidified brine.

It will be appreciated that transforming the oilfield fluid into a paste as described above may confer multiple advantages. For example, transforming the fluid into a paste may enable the XRF measurements to be performed under vacuum (or very low pressure) where the light elements such as sodium (Na) and Magnesium (Mg) may be measured more accurately. Moreover, transforming the fluid into a paste may enable longer measurement times to be employed (since pastes do not settle or otherwise separate), thereby improving signal to noise of the measurement. Transforming the drilling fluid into a paste may further enable robust and customized calibration procedures to be developed and utilized.

It will be further appreciated that making distinct XRF measurements of the total fluid (the paste) and the liquid component thereof (the brine) may advantageously enable a low-cost evaluation of the elemental composition of the solids to be estimated.

With continued reference to FIG. 6, it will be appreciated that the XRF measurements may be made automatically or semi-automatically, for example, as described above with respect to FIGS. 2 and 3. In such embodiments, XRF measurement systems 150 may be similar to XRF measurement system 150 depicted on FIG. 2.

Moreover, such automated or semi-automated XRF measurements may be used to automate or semi-automate the HGS solids recovery and dewatering processes depicted on FIG. 2. In one example embodiment in which XRF measurements are made on the supernatant of the HGS recovery centrifuge, the peak height or peak area of a predetermined peak (or peaks) in the XRF spectra may be automatically evaluated and used to control the drilling fluid flow rate into the centrifuge and/or the rotation rate of the centrifuge. For example, when the XRF spectra indicate that the quantity of HGS solids is above a threshold, the rotation rate of the centrifuge may be increased or the flow rate of drilling fluid into the centrifuge may be decreased to improve the efficiency of centrifuge.

In another example embodiment in which XRF measurements are made on the supernatant of the dewatering centrifuge, the peak height or peak area of a predetermined peak (or peaks) in the XRF spectra may be automatically evaluated and used to control the drilling fluid flow rate into the centrifuge and/or the rotation rate of the centrifuge. For example, when the XRF spectra indicate that the quantity of LGS solids is above a threshold, the rotation rate of the centrifuge may be increased or the flow rate of drilling fluid into the centrifuge may be decreased to improve the efficiency of centrifuge. Or when the XRF spectra indicate that the quantity of aluminum is above a threshold, the amount of coagulant added to the mixer may be reduced, and or the amount of flocculant may be increased. It will, of course, be appreciated that the disclosed embodiments are not limited to these example automated implementations.

Figure 7A:
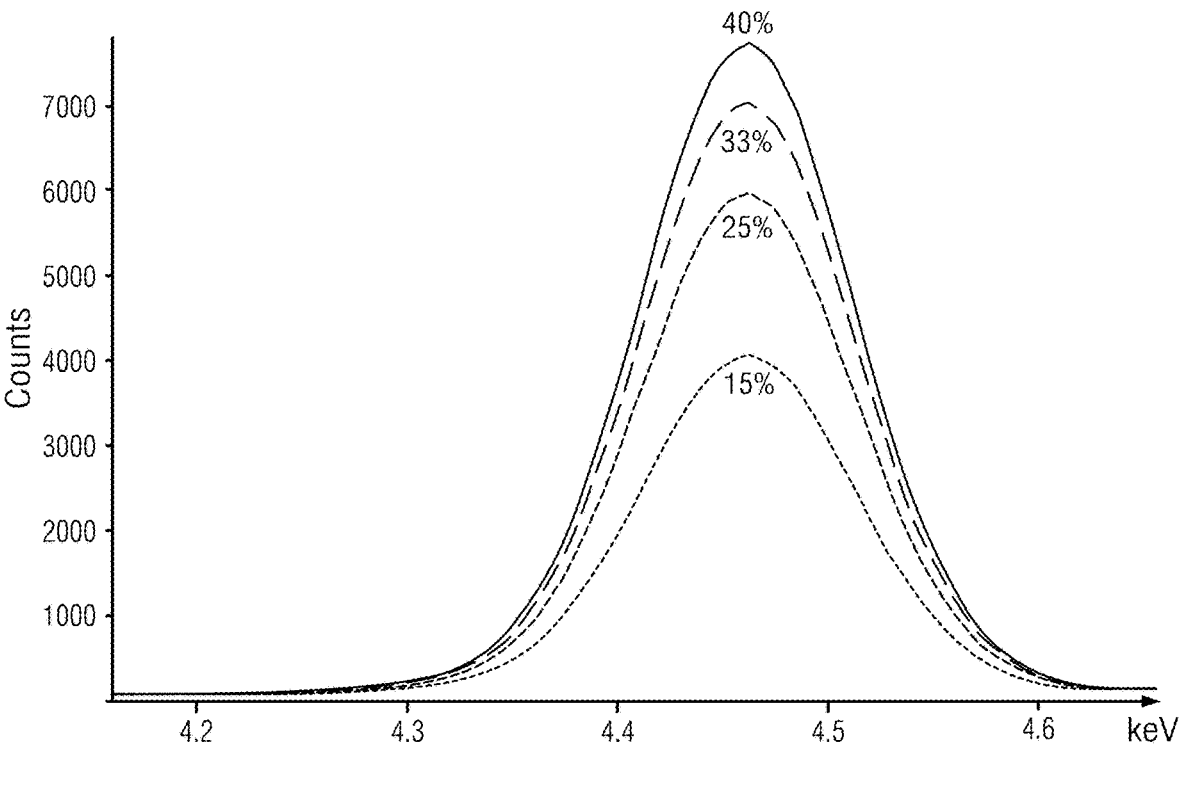
FIGS. 7A and 7B (collectively FIG. 7) depict portions of measured XRF spectra (XRF measurements) obtained from paste samples including drilling fluids and carbon black mixtures showing barium peaks (7A) and silicon peaks (7B).
Figure 7B:
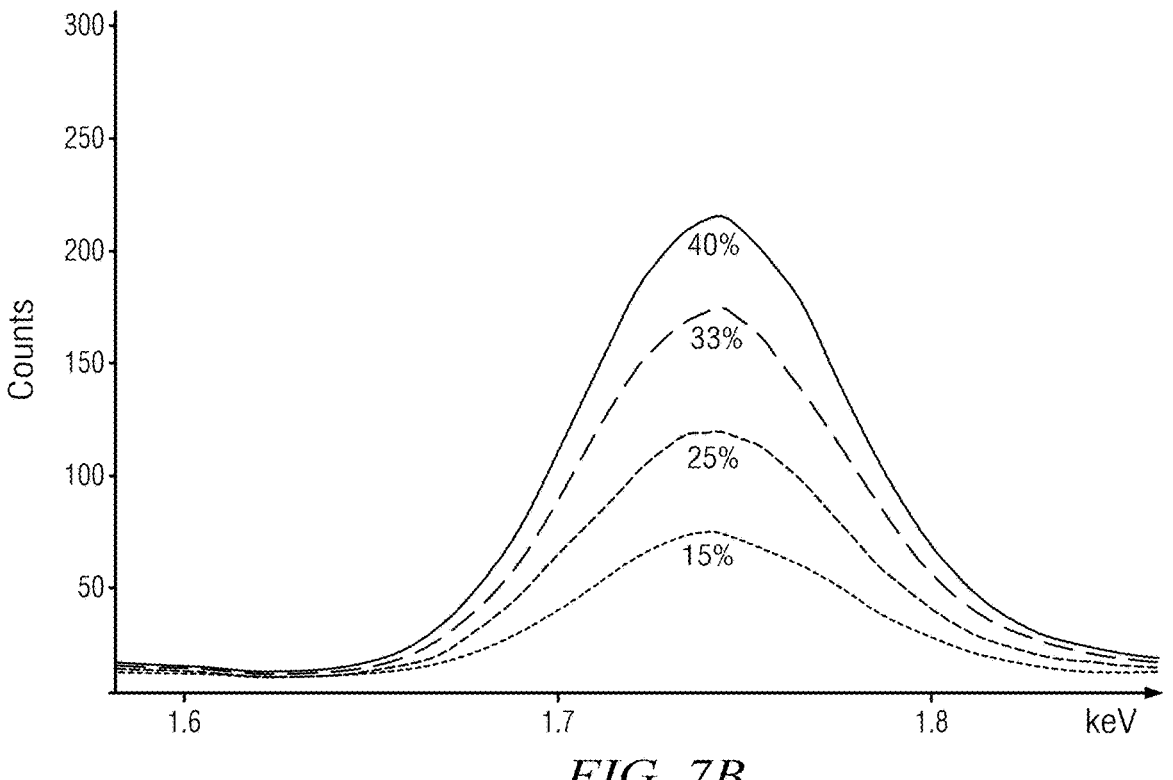

FIGS. 7A and 7B (collectively FIG. 7) depict portions of measured XRF spectra (XRF measurements) obtained from paste samples including drilling fluids and carbon black mixtures. Each paste sample was prepared by combining nine parts by weight of drilling fluid with one part by weight carbon black to form the paste. To obtain the spectra depicted on FIG. 7A, four water based drilling fluids were prepared including 15, 25, 33, and 40 weight percent barite, respectively. Corresponding paste samples were prepared and evaluated to obtain the depicted XRF spectra. Note that as expected the peak height of the barium Lαl peak increased with the increasing amount of barite in the drilling fluid.

To obtain the spectra depicted on FIG. 7B, four water based drilling fluids were prepared including 15, 25, 33, and 40 weight percent American Petroleum Institute (API) clay, respectively. Corresponding paste samples were prepared (by combining 9 parts by weight of drilling fluid with one part by weight carbon black) and evaluated to obtain the depicted XRF spectra. Note that as expected the peak height of the silicon Ka1 peak increases with an increasing amount of barite in the drilling fluid.

As indicated in FIG. 7, the elemental (e.g., barium or silicon) peak heights depend on both the concentration of the element in the drilling fluid and on the relative amount of carbon black used to form the paste (the peak height generally increases with an increasing amount of the element in the drilling fluid and generally decreases with an increasing amount of carbon black in the paste). It will be appreciated that reliable calibrations may be advantageously obtained for such paste samples. For example, the calibration may be obtained by evaluating a number of paste samples having known concentrations of various drilling fluid components (known elemental concentrations) and developing correlations between the observed peak heights (or areas under the peaks) and the known concentrations. Such calibrations may include Compton peak normalization or Compton/Rayleigh peak ratios as is known to those of ordinary skill. The disclosed embodiments are not limited to any particular calibration or calibration methodology.

The following synthetic example further illustrates example embodiments of the invention but, of course, should not be construed as in any way limiting its scope.

Table 1 lists an expected (or desired) mass balance for a drilling fluid used in an example drilling operation through a reservoir zone comprising intermixed layered zones including shales, dolomites, and anhydrite. The desired mass balance is listed as a composition of numerous components, including water, a calcium carbonate weighting agent, salt, and an amine based shale inhibitor among components. This particular drilling fluid is not intended to include a barite weighting agent. In an example drilling operation, a drilling engineer may be tasked with maintaining each component of the mud within an acceptable tolerance of the composition listed in Table 1.

TABLE 1

| Drilling Fluid Component | Target Composition (ppm) |
| --- | --- |
| Water | 710,000 |
| Calcium Carbonate | 150,000 |
| Driller Salt (NaCl) | 70,000 |
| Shale Inhibitor (Amine Based) | 30,000 |
| Phosphate Ester Lubricant | 20,000 |
| Polysaccharide Viscosifier | 5000 |
| Acrylamide Encapsulator | 5000 |
| Magnesium Breaker | 5000 |
| Lime | 5000 |

As described above with respect to FIGS. 3 and 4, a multiphase drilling fluid sample may be acquired (e.g., from a mud pit or fluid flow line). The sample may be transformed into a paste via blending with carbon black. A first XRF measurement of the paste may yield an elemental composition of the whole fluid, for example, as described above with respect to elements 206 and 256 of FIGS. 3 and 4. A second XRF measurement (taken after a calcimeter measurement and a fluid separation) may yield an elemental composition of an acidified brine, for example, as described above with respect to elements 216 and 268 of FIGS. 3 and 4. Example elemental compositions are listed in Table 2 (in units of ppm by mass). Table 2 also lists an estimated solid phase composition obtained by subtracting the brine composition from the whole fluid composition and the total carbonate concentration obtained from the calcimetry measurement.

TABLE 2

| Element | Whole Fluid (XRF1) | Acidified Brine (XRF2) | Solid Phase (Estimate) |
| --- | --- | --- | --- |
| Na | 29,000 | 27,000 | 2000 |
| Mg | 4500 | 4100 | 400 |
| Al | 11,000 | 100 | 10,900 |
| Si | 25,000 | 300 | 24,700 |
| Cl | 45,000 | 145,000 | 1000 * |
| Ca | 115,000 | 100,000 | 15,000 |
| Ba | 17,000 | 0 | 17,000 |
| Th | 1.5 | 0 | 1.5 |
| U | 6 | 0 | 6 |
| Br | 1400 | 1300 | 100 |
| $CO_3^{2-}$ | 170,000 | — | — |

* further subtracting Cl from HCl used in calcimetry measurement

Note that in this example, the composition of the solid phase may be advantageously estimated by subtracting the composition of the acidified brine from the composition of the whole fluid. Moreover, as described above, the estimated composition of the solid phase may be compared with XRF measurements on solids obtained from the separation.

In this particular example, the calcimetry measurement indicates 170,000 ppm carbonate, which is well in excess of the 90,000 ppm expected from the calcium carbonate weighting agent. The discrepancy may be the result of an error in calcium carbonate dosing or drilling through a carbonate rich formation.

The high aluminum and silicon concentrations in the whole fluid and the estimated solid phase may be indicative of LGS contamination in the mud and may also be indicative of siliceous and argillaceous minerals in the formation. The presence of thorium and uranium may be further evaluated, for example, by referring to logging measurements to indicate whether the wellbore has previously intersected or is currently drilling in a thorium or uranium containing formation. The levels of aluminum, silicon, thorium, and uranium may be monitored with time to determine whether these elements are the result of previous mud contamination or current formation. For example, a mud engineer may review the mud pit volumes, and valve working, to make sure that there is no influx of non-reservoir drilling fluids into the reservoir drilling fluid pit.

By monitoring the magnesium and calcium levels in the whole sample, the acidified filtrate, and the estimated solid phase, an engineer may recognize an excess of both elements compared to the values expected from the target composition of the mud and may further relate these values to a potential uptake of solids from the formation rather than to an error in the dosing of the magnesium based breaker and of the calcium carbonate based weighting agent. By further comparing the calcium content of the whole sample and the acidified filtrate, an engineer may interpret that a representative lower value of calcium in the filtrate may indicate the drilling process is taking place through an anhydrite formation.

Moreover, the presence of barium in the whole sample and solid phase may indicate that the formation may include an evaporite rich in barite, or more likely, that the mud is contaminated with HGS from a previous drilling zone.

It will be understood that the present disclosure includes numerous embodiments. These embodiments include, but are not limited to, the following embodiments.

In a first embodiment, a method for evaluating a composition of a multiphase oilfield fluid includes blending a first sample of the multiphase oilfield fluid with a viscosity modifying agent to transform the first sample into a paste; making a first XRF measurement of the paste to estimate an elemental composition of the multiphase oilfield fluid; making a calcimetry measurement of a second sample of the multiphase oilfield fluid to estimate a total carbonate concentration of the multiphase oilfield fluid and to obtain an acidified second sample; separating the acidified second sample to obtain an acidified brine; making a second XRF measurement of the acidified brine to estimate an elemental composition of the acidified brine; and determining an elemental composition of a solid phase of the multiphase oilfield fluid from the elemental composition of the acidified brine and the elemental composition of the multiphase oilfield fluid.

A second embodiment may include the first embodiment, wherein the making the calcimetry measurement further comprises acidifying the second sample; routing generated gas to a Draeger tube to measure a partial pressure of carbon dioxide; and estimating the total carbonate concentration from the partial pressure of carbon dioxide.

A third embodiment may include any one of the first through second embodiments, wherein the separating further comprises separating the acidified second sample to obtain an acidified brine and separated solids; and the method further comprises making a third XRF measurement of the separated solids to estimate an elemental composition of the separated solids.

A fourth embodiment may include the third embodiment, further comprising comparing the elemental composition of the solid phase of the multiphase oilfield fluid and the elemental composition of the separated solids.

A fifth embodiment may include any one of the first through fourth embodiments, further comprising adjusting the composition of the multiphase oilfield fluid based on the estimated composition of the solid phase of the multiphase oilfield fluid.

A sixth embodiments may include any one of the first through fifth embodiments, wherein the viscosity modifying agent is carbon black.

A seventh embodiment may include any one of the first through sixth embodiments, wherein the first and second samples of the multiphase oilfield fluid are automatically obtained from a flow line, a tank, or a mud pit; the first sample is automatically blended with the viscosity modifying agent to transform the first sample into the paste; and an auto-calcimetry measurement is automatically made on the second sample.

An eight embodiment may include any one of the first through seventh embodiments, wherein the multiphase oilfield fluid is a dewatering fluid obtained from a high gravity solids (HGS) recovery system in a drilling fluid dewatering process; and the method further comprises evaluating the solid phase of the multiphase oilfield fluid for at least one of barium, manganese, iron, or calcium to estimate an amount of HGS in the dewatering fluid.

A ninth embodiment may include the eighth embodiment, further comprising adjusting an operational parameter of the HGS recovery system in response to the estimated amount of HGS in the dewatering fluid.

A tenth embodiments may include any one of the first through ninth embodiments, wherein the multiphase oilfield fluid is a clean centrate fluid obtained from a low gravity solids (LGS) removal system in a drilling fluid dewatering process; and the method further comprises evaluating the solid phase of the multiphase oilfield fluid for at least one of calcium, magnesium, silicon, aluminum, thorium, or uranium to estimate an amount of LGS in the clean centrate fluid.

An eleventh embodiment may include the tenth embodiment, further comprising adjusting an operational parameter of the LGS removal system in response to the estimated amount of LGS in the clean centrate fluid.

In a twelfth embodiment a system for estimating a composition of a solid phase of a multiphase oilfield fluid includes a fluid input port configured for receiving samples of the multiphase oilfield fluid; a mixer configured to mix a first sample of the multiphase oilfield fluid with carbon black to transform the first sample to a paste; an auto-calcimeter configured to make an automatic calcimeter measurement of a second sample of the multiphase fluid to generate an acidified second sample; a separation apparatus configured to separate the acidified second sample and obtain an acidified brine and separated solids; an x-ray fluorescence (XRF) measurement tool configured to make a first XRF measurement of the paste and a second XRF measurement of the acidified brine; a processor configured to evaluate the first and second XRF measurements to estimate a composition of the solid phase of the multiphase oilfield fluid.

A thirteenth embodiment may include the twelfth embodiment, wherein the auto-calcimeter further comprises a chamber for receiving and acidifying the second sample; a pressure sensor configured to monitor a pressure of a generated gas in the chamber after acidifying the second sample; a valve configured to open when the pressure sensor senses a stabilizing pressure in the chamber, thereby routing the generated gas to a Draeger tube; and the Draeger tube configured to measure a partial pressure of carbon dioxide in the generated gas.

A fourteenth embodiment may include any one of the twelfth through thirteenth embodiments, further comprising a carbon black containing vessel configured to transfer the carbon black to the mixer.

A fifteenth embodiment may include any one of the twelfth through fourteenth embodiments, wherein the processor is further configured to evaluate the first XRF measurement to estimate an elemental composition of multiphase oilfield fluid; evaluate the second XRF measurement to estimate an elemental composition of the acidified brine; and subtract the elemental composition of the acidified brine from the elemental composition of the multiphase oilfield fluid to compute the composition of the solid phase of the multiphase oilfield fluid.

In a sixteenth embodiment a method for evaluating a dewatering fluid includes obtaining a sample of the dewatering fluid from a high gravity solids (HGS) recovery system or a low gravity solids (LGS) removal system in a dewatering process; blending a first portion of the sample with carbon black to transform the sample into a paste; making a first XRF measurement of the paste to estimate an elemental composition of the dewatering fluid; making a calcimetry measurement of a second portion of the sample to estimate a total carbonate concentration in the sample and to obtain an acidified second portion; separating the acidified second portion to obtain an acidified brine; making a second XRF measurement of the acidified brine to estimate an elemental composition of the acidified brine; and determining a composition of a solid phase of the dewatering fluid from the elemental composition of the acidified brine and the elemental composition of the dewatering fluid.

A seventeenth embodiments may include the sixteenth embodiment, wherein the dewatering fluid is obtained from the HGS recovery system; and the method further comprises evaluating the second XRF measurement for at least one of barium, manganese, iron, or calcium to estimate an amount of HGS in the dewatering fluid.

An eighteenth embodiment may include the seventeenth embodiment, further comprising adjusting an operational parameter of a centrifuge in the HGS recovery system in response to the estimated amount of HGS in the dewatering fluid.

A nineteenth embodiment may include any one of the sixteenth through eighteenth embodiments, wherein the dewatering fluid is obtained from the LGS removal system; and the method further comprises evaluating the second XRF measurement for at least one of calcium, magnesium, silicon, aluminum, thorium, or uranium to estimate an amount of LGS in the dewatering fluid.

A twentieth embodiment may include the nineteenth embodiment, further comprising adjusting an operational parameter of a centrifuge in the LGS removal system in response to the estimated amount of LGS in the dewatering fluid.

Although XRF and calcimetry evaluation of multiphase oil-field fluids has been described in detail, it should be understood that various changes, substitutions and alternations can be made herein without departing from the spirit and scope of the disclosure as defined by the appended claims.

What is claimed is:

1. A method for evaluating a composition of a multiphase oilfield fluid, the method comprising:

blending a first sample of the multiphase oilfield fluid with a viscosity modifying agent to transform the first sample into a paste;

making a first XRF measurement of the paste to estimate an elemental composition of the multiphase oilfield fluid;

making a calcimetry measurement of a second sample of the multiphase oilfield fluid to estimate a total carbonate concentration of the multiphase oilfield fluid and to obtain an acidified second sample;

separating the acidified second sample to obtain an acidified brine;

making a second XRF measurement of the acidified brine to estimate an elemental composition of the acidified brine; and determining an elemental composition of a solid phase of the multiphase oilfield fluid from the elemental composition of the acidified brine and the elemental composition of the multiphase oilfield fluid.

2. The method of claim 1, wherein the making the calcimetry measurement further comprises:

acidifying the second sample;

routing generated gas to a Draeger tube to measure a partial pressure of carbon dioxide; and estimating the total carbonate concentration from the partial pressure of carbon dioxide.

3. The method of claim 1, wherein:

the separating further comprises separating the acidified second sample to obtain the acidified brine and separated solids; and the method further comprises making a third XRF measurement of the separated solids to estimate an elemental composition of the separated solids.

4. The method of claim 3, further comprising comparing the elemental composition of the solid phase of the multiphase oilfield fluid and the elemental composition of the separated solids.

5. The method of claim 1, further comprising adjusting the composition of the multiphase oilfield fluid based on the estimated composition of the solid phase of the multiphase oilfield fluid.

6. The method of claim 1, wherein the viscosity modifying agent is carbon black.

7. The method of claim 1, wherein:

the first and second samples of the multiphase oilfield fluid are automatically obtained from a flow line, a tank, or a mud pit;

the first sample is automatically blended with the viscosity modifying agent to transform the first sample into the paste; and an auto-calcimetry measurement is automatically made on the second sample.

8. The method of claim 1, wherein:

the multiphase oilfield fluid is a dewatering fluid obtained from a high gravity solids (HGS) recovery system in a drilling fluid dewatering process; and the method further comprises evaluating the solid phase of the multiphase oilfield fluid for at least one of barium, manganese, iron, or calcium to estimate an amount of HGS in the dewatering fluid.

9. The method of claim 8, further comprising adjusting an operational parameter of the HGS recovery system in response to the estimated amount of HGS in the dewatering fluid.

10. The method of claim 1, wherein:

the multiphase oilfield fluid is a clean centrate fluid obtained from a low gravity solids (LGS) removal system in a drilling fluid dewatering process; and the method further comprises evaluating the solid phase of the multiphase oilfield fluid for at least one of calcium, magnesium, silicon, aluminum, thorium, or uranium to estimate an amount of LGS in the clean centrate fluid.

11. The method of claim 10, further comprising adjusting an operational parameter of the LGS removal system in response to the estimated amount of LGS in the clean centrate fluid.

12. A system for estimating a composition of a solid phase of a multiphase oilfield fluid, the system comprising:

a fluid input port configured for receiving samples of the multiphase oilfield fluid;

a mixer configured to mix a first sample of the multiphase oilfield fluid with carbon black to transform the first sample to a paste;

an auto-calcimeter configured to make an automatic calcimeter measurement of a second sample of the multiphase oilfield fluid to generate an acidified second sample;

a separation apparatus configured to separate the acidified second sample and obtain an acidified brine and separated solids;

an x-ray fluorescence (XRF) measurement tool configured to make a first XRF measurement of the paste and a second XRF measurement of the acidified brine; and a processor configured to evaluate the first and second XRF measurements to estimate a composition of the solid phase of the multiphase oilfield fluid.

13. The system of claim 12, wherein the auto-calcimeter further comprises:

a chamber for receiving and acidifying the second sample;

a pressure sensor configured to monitor a pressure of a generated gas in the chamber after acidifying the second sample;

a valve configured to open when the pressure sensor senses a stabilizing pressure in the chamber, thereby routing the generated gas to a Draeger tube; and the Draeger tube configured to measure a partial pressure of carbon dioxide in the generated gas.

14. The system of claim 12, further comprising a carbon black containing vessel configured to transfer the carbon black to the mixer.

15. The system of claim 12, wherein the processor is further configured to:

evaluate the first XRF measurement to estimate an elemental composition of the multiphase oilfield fluid;

evaluate the second XRF measurement to estimate an elemental composition of the acidified brine; and subtract the elemental composition of the acidified brine from the elemental composition of the multiphase oilfield fluid to compute the composition of the solid phase of the multiphase oilfield fluid.

16. A method for evaluating a dewatering fluid, the method comprising:

obtaining a sample of the dewatering fluid from a high gravity solids (HGS) recovery system or a low gravity solids (LGS) removal system in a dewatering process;

blending a first portion of the sample with carbon black to transform the sample into a paste;

making a first XRF measurement of the paste to estimate an elemental composition of the dewatering fluid;

making a calcimetry measurement of a second portion of the sample to estimate a total carbonate concentration in the sample and to obtain an acidified second portion;

separating the acidified second portion to obtain an acidified brine;

making a second XRF measurement of the acidified brine to estimate an elemental composition of the acidified brine; and determining a composition of a solid phase of the dewatering fluid from the elemental composition of the acidified brine and the elemental composition of the dewatering fluid.

17. The method of claim 16, wherein:

the dewatering fluid is obtained from the HGS recovery system; and the method further comprises evaluating the second XRF measurement for at least one of barium, manganese, iron, or calcium to estimate an amount of HGS in the dewatering fluid.

18. The method of claim 17, further comprising adjusting an operational parameter of a centrifuge in the HGS recovery system in response to the estimated amount of HGS in the dewatering fluid.

19. The method of claim 16, wherein:

the dewatering fluid is obtained from the LGS removal system; and the method further comprises evaluating the second XRF measurement for at least one of calcium, magnesium, silicon, aluminum, thorium, or uranium to estimate an amount of LGS in the dewatering fluid.

20. The method of claim 19, further comprising adjusting an operational parameter of a centrifuge in the LGS removal system in response to the estimated amount of LGS in the dewatering fluid.

*　*　*　*　*